United States Patent [19]

Thomas et al.

[11] 4,383,391
[45] May 17, 1983

[54] SEED COATING COMPOSITION BASED ON CARBAMATE PESTICIDE AND NON-ALKALINE AMORPHOUS CARBON

[75] Inventors: Norman W. Thomas, Somerset, N.J.; Henry A. Terwedow, DuPage, Ill.

[73] Assignee: Celanese Corporation, New York, N.Y.

[21] Appl. No.: 303,818

[22] Filed: Sep. 21, 1981

[51] Int. Cl.³ .............................................. A01C 1/06
[52] U.S. Cl. .................................... 47/57.6; 424/125; 424/285
[58] Field of Search ................. 47/57.6; 424/122, 125, 424/285

[56] References Cited

U.S. PATENT DOCUMENTS 2,671,985  3/1954  Vogelsang ........................ 47/57.6
3,519,709  7/1970  Addor ............................ 47/57.6 X
3,648,409  3/1972  Johnson et al. ................... 47/57.6

*Primary Examiner*—Robert E. Bagwill
*Attorney, Agent, or Firm*—Scully, Scott, Murphy & Presser

[57] ABSTRACT

The phytoxicity of a carbamate pesticide such as carbofuran (2,3-dihydro-2,2-dimethyl-7-benzofuranol methylcarbamate) contained in a seed coating composition is nullified or minimized without materially reducing the pesticidal effectiveness of the carbamate by the presence in the seed coating composition of an activiated charcoal powder of neutral to acid pH.

14 Claims, No Drawings

SEED COATING COMPOSITION BASED ON CARBAMATE PESTICIDE AND NON-ALKALINE AMORPHOUS CARBON

BACKGROUND OF THE INVENTION

1. Field of the Invention

This invention belongs to the field of seed coating compositions containing a pesticide and, more particularly, to such compositions containing a pesticidal carbamate as the active ingredient.

2. Description of the Prior Art

Carbamates of dihydrobenzofuranols (U.S. Pat. Nos. 3,356,690 to Orwoll; 3,474,170 to Scharpf; and, 3,474,171 to Scharpf) of which carbofuran is a well-known commercially available representative (FMC Corporation's Furadan) are pesticide substances effective against a wide variety of crop-destroying insects, nematodes, etc., whether applied to soil or to the above ground parts of growing plants. The carbamates are generally formulated with other compatible materials such as particulate carriers, wetting agents, dispersants, and the like, which facilitate their use. However, direct contact of carbofuran and other carbamate pesticides is known to cause severe damage to some types of seed.

U.S. Pat. No. 3,545,129 to Schreiber describes a multiple coating for seed having (a) an inner coating which is permeable to water, (b) an intermediate coating which is semipermeable to water, and (c) an outer coating which is substantially impermeable to moisture but is fissionable at frost temperatures. The inner coating contains a coating material such as powdered charcoal, a binder and a plasticizer. Nothing is said in this patent regarding the use of a non-alkaline powdered charcoal.

It is known from the literature relating to the agricultural use of activated charcoal (viz. Linscott, et al., *Weeds*, 15 (1967), pp. 304–306; Andersen, *Weed Res.*, 8 (1968), pp. 58–60; Andersen, *Weed Res.*, 9 (1969), pp. 254–257; and, Moyer, et al., *Soil Biol. Biochem.*, Pergamon Press (1972), Vol. 4, pp. 307–311) that charcoal, or amorphous carbon applied to soil or furrow, protects seeds from injury due to various pesticides.

Heretofore, there has been no recognition or appreciation that charcoals such as alkaline Norit (American Norit Co., Inc.) can significantly counteract the effectiveness of the carbamate family of pesticides.

SUMMARY OF THE INVENTION

It has now been observed that alkaline powdered charcoals, while effective in reducing the phytotoxicity of the carbamate pesticides, tend to redude the effectiveness of these pesticides. Surprisingly, it has been discovered that if a seed coating composition is formulated with a non-alkaline charcoal, i.e., a charcoal which is in the neutral to acid pH range, protection of the coated seeds from the phytotoxic effects of carbamate pesticide will be achieved without a measurable loss in pesticidal effectiveness of the carbamate. The practical consequence of this discovery is to permit the formulation of pesticidally active seed coating compositions which provide effective levels of pesticidal protection but with reduced levels of both the active pesticide ingredient as well as the phytotoxic-protective ingredient.

Thus, in accordance with the present invention, a continuous adherent seed coating composition is provided which comprises:

(a) a first layer in adherent contact with a seed surface containing as the major component by weight thereof, a phytotoxic-protective amount of a particulate activated charcoal of substantially neutral to acidic pH, the charcoal being bound to the seed surface with a binding amount of a non-phytotoxic binder; and, (b) a second layer in adherent contact with the outer surface of the first layer containing a pesticidally effective amount of a carbamate pesticide, the carbamate pesticide being bound to the outer surface of the first layer with a binding amount of a non-phytotoxic binder.

As used herein the terms "charcoal" and "carbon" are to be understood as equivalent.

DESCRIPTION OF THE PREFERRED EMBODIMENTS

Any of the substantially neutral to acidic activated charcoal powders can be used herein, advantageously those having a pH of from about 4 to about 7. Commercially available charcoals include neutral Norit A (American Norit Co., Inc.) which, as its name implies, possesses a pH of about 7, and Darco G-60 (Atlas Chemical Industries, Inc.) which possesses a pH of from about 4 to about 7.

The amount of charcoal powder required to adequately protect the seed from the phytotoxic effects of the carbamate pesticide depends largely upon the concentration of the latter in the seed coating composition. In general, an appreciable level of protection can be achieved with a weight ratio of charcoal to carbamate of from about 1:10 to about 50:1, preferably from about 1:1 to about 10:1.

Any of the known and conventional non-phytotoxic binders employed in seed coating compositions can be utilized herein. Preferably, the binders are of the water soluble or water dispersible type although it will be understood that emulsion type binders, for example, latices of polyvinyl acetate, can also be used herein with acceptable results. Included amongst the water soluble and water dispersible binders, in a suitable solvent carrier, e.g., water and/or alcohol, are Gelvatol 20–30 (Monsanto), a polyvinyl alcohol resin (about 10,000 average molecular weight, 85–89 percent hydrolyzed, to a residual acetate content of 20–25 weight percent), PVPK-30 (GAF Corporation), a polyvinylpyrrolidone, poly (caprolactone), methyl cellulose, hydroxypropyl cellulose, dextrins, sugar molasses, alginates, karaya gum, jaguar gum, tragacanth gum, polysaccharide gum, natural glue, mucilage, and the like. The amount of binder, exclusive of carrier, should be as small as possible consistent with the mechanical integrity necessary for shipping, handling and planting of the coated seed. The amount of a particular binder which is used to adhere the charcoal powder to the seed surface will depend upon its adhesive properties and generally will not exceed about 10% of the charcoal layer by weight. Advantageously, from about 3 to 5% binder can be utilized with good results.

Some types of seeds, notably soybean seeds, exhibit a marked tendency to readily swell in the presence of water and contract upon drying. This tendency varies somewhat with the nature of the soybean seeds, depending on the particular cultivar and probably also on the history of the particular seed lot. The differential expansion and contraction produces a puckered seed coating and leads to a tendency for the coatings to crack. The use of adhesives of relatively high osmotic pressure has been found to minimize this problem for aqueous binder systems and as such, constitutes a particular feature of the present invention. Such relatively high osmotic pressures as are useful in overcoming this expansion/contraction tendency include high solids, e.g., 20% weight aqueous solutions, of 10,000–40,000 average molecular weight polyvinyl alcohols and polyvinylpyrrolidones.

Water insoluble or non-water dispersible binders in a suitable organic solvent can also be used herein. Such binders include cellulose esters, e.g., cellulose acetate, which are preferred. The selected solvent can, if desired, be a mutual solvent for the carbamate pesticide. The solvent which is selected for a particular seed and seed coating composition must, of course, not adversely affect the viability of the seed in any significant way. Solvents which can be used in preparing the coated seeds herein include such halogenated hydrocarbon solvents as chloroform, methylene chloride, 1,1,1-trichlorethane, trichlorofluoromethane, dimethylformamide, ethers, especially diethylether, ketones, especially acetone, and the like. Combinations of these and other solvents can also be used. Thus, in the case of cellulose acetate ester, a mixture of methylene chloride and methanol provides an entirely suitable solvent system for this binder. The quantity of organic solvent employed should generally be only so much as is needed to provide a suitable adhesive mediu. To the extent less solvent is employed, shorter drying times are required to provide the seed coating compositions herein. Binder to solvent weight ratios can vary in most instances from about 1:1 to about 1:10. Optimum ratios, will, of course, depend upon the particular binder/solvent system chosen.

The carbamate pesticides which can be used in the seed coating compositions of this invention constitute, together with their derivatives, a well known class of materials. The carbamates and their method of preparation are the subject of U.S. Pat. Nos. 3,356,690 to Orwoll; 3,474,170 to Scharpf; and 3,474,171 to Scharpf, each of which is incorporated by reference herein. The carbamates and their analogues can be represented by the general formulae

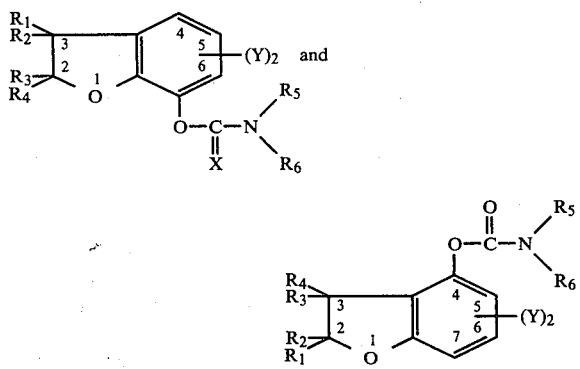

wherein $R_1$, $R_2$, $R_3$ and $R_4$ are each hydrogen or aliphatic groups of one to about three carbon atoms including alkyl and alkenyl groups: $R_5$ and $R_6$ are each hydrogen or aliphatic groups of one to about three carbon atoms, including alkyl, alkenyl and alkynyl groups; and X is oxygen or sulfur. These compounds may be unsubstituted in the benzene ring, or may contain one or more substitutents Y in the benzene ring as shown where n is an integer of 1 to 3, which substitutents Y may be the same or different and may be lower aliphatic groups, including alkyl and alkenyl groups halogen, haloalkyl, nitro, amino and substituted amino, cyano, alkoxy carbonyl, acyl, alkymercapto, alkoxy, other carbamate groups and the like.

Especially preferred, however, is the carbamate carbofuran as this pesticide has been cleared for use and is commercially available (Furadan, FMC Corporation, Agricultural Chemical Division). Carbofuran in the pure state is a white cyrstalline solid (m.p. 150°–153° C.) and can be represented by the formula

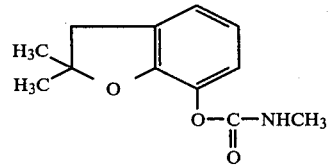

Chemically, carbofuran is variously named 2,3-dihydro-2,2-dimethyl-7-benzofuranol methylcarbamate; methyl carbamic acid 2,3-dihydro-2,2-dimethyl-7-benzofuranyl ester, 2,2-dimethyl-2,3-dihydro-7-benzofuranyl-N-methylcarbamate; and 2,2-dimethyl-7-coumaranyl N-methycarbamate.

Carbofuran is effective in the protection of corn, peanuts, peppers, sorghum, sugar beets, sugar cane, tobacco, alfalfa, rice, banana and numerous other plants from pesticidal attack. Among the pests for which carbofuran is toxic are included corn rootworms, flea beetles, armyworm, nematodes, wireworm, hornworms, and so forth.

The binders employed in adhering the carbamate pesticide to the carbamate layer of the seed coating compositions herein can be selected from among any of the previously cited binders employed in adhering the charcoal layer to the seed surface. Convenience favors the use of the same binder, e.g., polyvinyl alcohol or polyvinylpyrrolidone, used in binding the charcoal powder to the seed.

The amount of carbamate pesticide which is present in solution or dispersion with the binder is calculated to provide in the finished granular product an effective level of pesticidal activity. Thus, for example, levels of carbamate of from about 0.5 to about 5.0 weight percent, and advantageously from about 1.0 to about 3.0 weight percent, by weight of seed coating composition generally provide entirely acceptable results. It is understood, however that quantities of carbamate less than, or in excess of, this amount can also be used with good effect.

It is also within the scope of this invention to include in the coating compositions customary amounts of additional ingredients as, for example, growth regulants, such as kinetin, fusicoccin, gibberellic acid, morphactin, aminotriazole, 2-chloroethylphosphonic acid, and the like (often applied directly to the seed surfaces in a preliminary soaking operation); particulate "hydrophobes", i.e., materials such as silanized silica, polyolefin, polyvinyl, polystyrene, natural and synthetic waxes, fluorocarbon polymers, and the like, which are not wetted by water to any appreciable extend; inert particulate fillers such as clays, silicates, diatomaceous earth, flyash, chalk, limestone, vermiculite, peat moss and the like; fertilizers; fungicidals; bacterial inoculants, nutrients, and so forth. These materials can be applied directly to the seed surface, they can be part of the first and/or second layers of the coating composition, and/or they can be applied to the exterior surface of either or both the first and second layers.

The average particle size of the particulate ingredients used to form the seed coatings, e.g., the charcoal powder, can vary within wide limits depending upon the type of seed to be coated. As will be readily appreciated, the effectiveness of the charcoal in inhibiting the phytotoxic character of the carbamate will generally be enhanced by using a charcoal having a relatively high average surface area, or, put in another way, relatively samll average particle size. It is generally advantageous for the particles of the various coating components (where such exist in particulate form) to be smaller than the seed so as to provide satisfactory buildup of the coating around the seed. To coat common vegetable seeds such as lettuce, sugar beet, radish, onion, celery, cucumber, carrot, spinach, tomato, cabbage, and the like, which seeds generally range in size from about 1 to 10 mm at their largest dimension, spherical, spheroidal or irregularly-shaped particles in the average size range of from about 5 millimicrons to about 900 microns can be used. It is preferred to use fine spheroidal particles in the size range of up to about 250 microns. When extremely small seeds, such as many of the flower seeds, are to be coated, it is advantageous to begin the coating operation with small particles and complete the coating with larger particles. For a given seed coating formulation, the nature of the pesticide and the charcoal, and the levels at which these ingredients are present, may suggest the use of such components having a particular range of particle size and/or in a particular amount if optimum protection from the phytotoxic effects of the pesticide is to be realized. In such a case, simple and routine experimentation will readily identify such ranges of ingredient particle size/amount which are most effective for a particular application.

The coatings are built up on the seeds employing known in conventional techniques such as pan-coating or spraying the binder dissolved in a solvent or carrier such as water onto a mixture of the seed and the particulate material rotating in a mixer of conventional type. Another useful process is the Wurster Air Suspension Coating Process which is described in U.S. Pat. Nos. 2,799,241; 3,089,824; 3,117,027; 3,196,827; 3,207,824; 3,241,520; and 3,253,994.

Advantageously, the concentration of optional hydrophobe, where used, in the mixture of coating materials can be adjusted toward the end of the coating operation to provide a greater amount of hydrophobe on the exterior surface of the seed coating where it has been found to be most effective. If employed as a component of the first layer, the hydrophobe shall be at most only a minor component by weight thereof.

The following example is illustrative of a seed coating composition prepared in accordance with this invention applied to soybean seed.

I. COATING SOYBEAN SEEDS WITH NON-ALKALINE CHARCOAL POWDER AND CARBOFURAN

A. Charcoal Powder Layer 200 gm of soybean seeds were tumbled in a stainless steel coater and while tumbling were wetted with 2 gm of a 20% by weight aqueous solution of Gelvatol 20-30 (Monsanto), a polyvinyl alcohol of about 10,000 average molecular weight. Thereafter, 2 gm Darco G-60 (Atlas Chemical Industries, Inc.), an activated charcoal having a pH of from about 4 to about 7, and 3 gm of the aforesaid Gelvatol 20-30 solution were successively added to the tumbling seeds followed by air-drying. The seeds thus coated contained approximately 1% by weight Darco G-60.

B. Carbofuran Layer 101 gm of the above charcoal coated seeds were placed in a pancoater. While tumbling, the seeds were wet with 2 gm of the Gelvatol 20-30 solution used in step A. Thereafter, 0.67 gm carbofuran (Furadan 75 DB powder from FMC Corporation, Agricultural Chemical Division, to provide 0.5% by weight of active ingredient on the seeds) were added to the tumbling seeds and the seeds were then airdried.

In the foregoing manner, the soybean seeds were provided with an adherent coating comprising an interior layer of non-alkaline charcoal and an external layer of carbofuran. Following substantially the same procedure, soybean seeds were coated with an alkaline charcoal, Norit A (American Norit Co., Inc.), and carbofuran. These coated seeds were then evaluated by bioassay with soybean seeds coated with Darco G-60 and Norit A alone serving as controls. The bioassay procedure and results are set forth in the following example.

II. BIOASSAY OF SOYBEAN SEEDS COATED WITH NON-ALKALINE CHARCOAL POWDER AND CARBOFURAN

A. Soil

Greenhouse plantings were made in an artificial soil mix consisting of white and yellow horticultural sand and potting soil in proportions of 4:4:3, together with small amounts (less than 1% by weight each) of agricultural lime and a 5:10:10:2 fertilizer mix. A typical 10"×10"×2" greenhouse tray held about five pounds of this mix.

B. Insects

Mexican bean beetle (obtained from Boyce Thompson Institute, Yonkers, N.Y.).

C. Insect Bioassay

Soybean seeds, one to a pot, were planted in small plastic pots. After the appropriate growing period, individual plants were challenged with five 2nd instar mixican bean beetle larvae and mortality was scored at 72 hours. Each treatment was replicated three times.

D. Plant Assay and Parameters

Fifteen coated seeds were sown per flat in three rows and each treatment replicated five times, i.e., a total of seventy five seeds/treatment sown over five flats. Stand counts were made at one, two, three and four week periods; the maximum number of plants emerged was used to note germination, recorded as percent of sown seed, as shown in the data set forth below. Degree of leaf burn is largely a subjective evaluation and necessitates that comparisons be made for plants grown at the same time. For example, for soybean light intensity can materially influence the apparent degree of burn so that observations made in a winter greenhouse are not the same as those made in a growth chamber with high intensity lighting, or in a summer greenhouse. The following scale for leaf burn was employed:

None (N)—No apparent burn.

Very Slight (VSL)—A series of small brown spots about the size of a pinhead on the outer edge of the leaf, i.e., "tip" burn.

Slight (SL)—Burning somewhat more intensive than tip burn or tip burn plus some puckering of the leaf.

Moderate (M)—Burning symptoms may be of the order of 10% of the leaf area.

Severe (S)—Burning up to 20% of the leaf. Very Severe (VS)—Burning greater than 20% of leaf area. In an extreme situation, the entire leaf is brown and desiccated.

The observations for degree of leaf burn were made throughout but the data given below refer to weighting of burning on first and second true leaf stages at four weeks.

For dry shoot weight, the plants in each flat were cut off (at four weeks) at the soil line, dried in an oven at 100° C. overnight and weighed; the average weight was obtained by dividing the number of plants per flat into weight per flat and then averaging again over five flats per treatment.

Results

The results of the bioassay were as follows:

|  | PLANT CHARACTERISTICS | | | % MORTALITY OF MEXICAN BEAN BEETLE PLANT AGE (Weeks) | | | |
|---|---|---|---|---|---|---|---|
| SEED COATING COMPOSITION (% by weight raw seed) | % Germination | Degree of Leaf Burn | Average Dry Shoot weight (gm) | 3 | 6 | 9 | 12 |
| FIRST EXPERIMENT (no artificial light, fall greenhouse) | | | | | | | |
| 50% Norit A | 96 | N | .90 | | | | |
| 50% Norit A + 0.5% carbofuran | 91 | N | .89 | 57.4 | | | |
| 50% Darco G-60 | 92 | N | .92 | | | | |
| 50% Darco + 0.5% carbofuran | 85 | N | .91 | 100 | | | |
| 0.5 Weight % carbofuran | 93 | VS | .76 | 100 | | | |
| seed | 96 | N | .72 | 10 | | | |
| SECOND EXPERIMENT (no artificial light, winter greenhouse) | | | | | | | |
| seed | 97 | N | .24 | 3.8 | 8.2 | 0 | 13.3 |
| 0.5% carbofuran | 91 | S | .21 | 100 | 92.9 | 88.1 | 60.8 |
| 1% Darco G-60 | 88 | N | .25 | 17.2 | 9.7 | 2.8 | 9.1 |
| 1% Darco G-60 + 0.5% carbofuran | 92 | S | .20 | 100 | 100 | 73 | 94.9 |
| 2.5% Darco G-60 | 93 | N | .25 | 21.7 | 10 | 0 | 13.3 |
| 2.5% Darco G-60 + 0.5% carbofuran | 76 | S-M | .21 | 100 | 100 | 41.2 | 47.5 |
| 5% Darco G-60 | 89 | N | .25 | 22.8 | 3.2 | 3.2 | 17.5 |
| 5% Darco G-60 + 0.5% carbofuran | 89 | M-SL | .20 | 100 | 100 | 82.1 | 40 |
| 12.5% Darco G-60 | 92 | N | .24 | 43.1 | 10.6 | 1.5 | 12.9 |
| 12.5% Darco G-60 + 0.5% carbofuran | 83 | SL | .19 | 100 | 100 | 75.8 | 88 |
| 25% Darco G-60 | 81 | N | .24 | 18 | 10.5 | 3.7 | 9.6 |
| 25% Darco G-60 + 0.5% carbofuran | 84 | VSL | .21 | 100 | 95.4 | 82.5 | 53.3 |
| 1% Norit A | 97 | N | .25 | 8.2 | 7.3 | 3.3 | 15.7 |
| 1% Norit + 0.5% carbofuran | 91 | S-M | .20 | 100 | 95 | 97 | 48.5 |
| 2.5% Norit A | 92 | N | .25 | 0 | 19.6 | 8.6 | 21.7 |
| 2.5% Norit A + 0.5% carbofuran | 91 | M | .21 | 100 | 83.3 | 56.1 | 39.2 |
| 5% Norit A | 84 | N | .24 | 1.7 | 21.7 | 22.6 | 31.7 |
| 5% Norit A + 0.5% carbofuran | 96 | SL | .22 | 95.2 | 67.3 | 38.3 | 22 |
| 12.5% Norit A | 65 | N | .23 | 3.2 | 6 | 6.9 | 3.3 |
| 12.5% Norit A + 0.5% carbofuran | 83 | N | .22 | 79.1 | 46.7 | 33.3 | 38.7 |
| 25% Norit A | 48 | N | .23 | 0 | 10 | 8 | 26.7 |
| 25% Norit A + 0.5% carbofuran | 64 | N | .24 | 35.8 | 41.1 | 31.7 | 8.8 |

The above data were obtained from two experiments, the first of which was carried out in natural sunlight under fall planting conditions. The second, more extensive study was carried out in a winter greenhouse without benefit of artificial light. This was a stressful situation since soybean is sensitive to changes in light intensity. All of the plants (28 days) in the second experiment were small relative to the more favorable fall conditions (Experiment (1)). There was some tendency for plant weight to be affected by carbofuran although the change in itself would not be expected to be highly detrimental. However, the benefit ascribed to use of charcoal was its substantial effect on leaf burn at levels of about 10:1 (charcoal to carbofuran). Plants with severe to very severe burning will not survive in the field. Levels above about 20:1 (charcoal to carbofuran) reduced insect control and use of alkaline charcoal at any level led to rapid loss of insect control with plant age due, it is believed, to degradation of the pesticide component.

What is claimed is:

1. A continuous, adherent coating composition for seeds comprising:
   (a) a first layer in adherent contact with the seed surface containing as the major component by weight thereof, a phytotoxic-protective amount of a particulate activated charcoal of substantially neutral to acidic pH, the charcoal being bound to the seed surface with a binding amount of a non-phytotoxic binder; and,
   (b) a second layer in adherent contact with the outer surface of the first layer containing a pesticidally effective amount of a carbamate pesticide, the carbamate pesticide being bound to the outer surface of the first layer with a binding amount of a non-phytotoxic binder.

2. The coating composition of claim 1 wherein the pH of the charcoal powder is in the range of from about 4 to about 7.

3. The coating composition of claim 1 wherein the charcoal possesses an average particle size range of from about 5 millimicrons to about 900 microns.

4. The seed coating composition of claim 1 wherein the binder is of the water soluble or water dispersible type.

5. The seed coating composition of claim 4 wherein the binder for the charcoal is an aqueous polyvinyl acetate latex or a water and/or alcohol solution or dispersion of polyvinyl alcohol, polyvinylpyrrolidone, methyl cellulose, hydroxylpropyl cellulose, a dextrin, sugar, molasses, an alginate, karaya gum, jaguar gum, tragacanth gum, polysaccharide gum, natural glue or mucilage.

6. The seed coating composition of claim 5 wherein the binder is a high solids content aqueous solution of a polyvinyl alcohol or polyvinylpyrrolidone having an average molecular weight of from about 10,000 to about 40,000.

7. The seed coating composition of claim 1 wherein the binder for the charcoal is an organic solvent solution of a water insoluble, non-water dispersible binder.

8. The seed coating composition of claim 1 wherein the binder is a cellulose ester or a poly (caprolactone).

9. The seed coating composition of claim 1 wherein the carbamate pesticide is carbofuran.

10. The seed coating composition of claim 1 wherein the binder for the carbamate is an aqueous polyvinyl acetate latex or a water and/or alcohol solution or dispersion of polyvinyl alcohol, polyvinylpyrrolidone methyl cellulose, hydroxylpropyl cellulose, a dextrin, sugar, molasses, an alginate, karaya gum, jaguar gum, tragacanth gum, polysaccharide gum, natural glue or mucilage.

11. The seed coating composition of claim 10 wherein the binder for the carbamate is a high solids content aqueous solution of a polyvinyl alcohol or polyvinylpyrrolidone having an average molecular weight of from about 10,000 to about 40,000.

12. The seed coating composition of claim 10 wherein the binder for the carbamate is an organic solvent solution of a water insoluble, non-water dispersible binder.

13. The seed coating composition of claim 10 wherein the binder is a cellulose ester of a poly (caprolactone).

14. The seed coating composition of claim 1 wherein the coating composition contains at least one additional ingredient selected from the group consisting of growth regulant, particulate hydrophobe, inert particulate filler, fertilizer, fungicide, bacterial inoculant and nutrient applied directly to the seed surface, as part of the first and/or second layer and/or applied to the exterior surface of either or both the first and second layers.

* * * * *